(12) United States Patent
Josefek

(10) Patent No.: US 9,504,595 B2
(45) Date of Patent: Nov. 29, 2016

(54) INFLATABLE COMPRESSION WRAP FOR DIRECT SUPPORT OF THE SPINOUS PROCESS IN THE LUMBAR SPECIFIC SPINE REGION

(71) Applicant: Kirt L. Josefek, Natick, MA (US)

(72) Inventor: Kirt L. Josefek, Natick, MA (US)

(73) Assignee: Kirt L. Josefek, Natick, MA (US)

( * ) Notice: Subject to any disclaimer, the term of this patent is extended or adjusted under 35 U.S.C. 154(b) by 348 days.

(21) Appl. No.: 14/018,991

(22) Filed: Sep. 5, 2013

(65) Prior Publication Data

US 2015/0065933 A1    Mar. 5, 2015

(51) Int. Cl.
*A61F 5/00*    (2006.01)
*A61F 5/02*    (2006.01)

(52) U.S. Cl.
CPC .................... *A61F 5/028* (2013.01)

(58) Field of Classification Search
CPC ............ A61F 2007/0056; A61F 7/02; A61F 2007/0018; A61F 2007/0054; A61F 2007/0228; A61F 2007/0296; A61F 7/007; A61F 5/028; A61F 7/106; A61F 2007/0029; A61F 2007/0039; A61F 2007/0002; A61F 2007/0027; A61F 2007/0058; A61F 2007/0076; A61F 2007/0225; A61F 13/20; A61F 13/26; A61F 2002/30617; A61F 2002/3071; A61F 2250/0059; A61F 2250/0067; A61F 2250/0068; A61F 2250/0085; A61F 2250/0097; A61F 2/0027; A61F 2/004; A61F 2/08; A61B 17/1355; A61B 17/42; A61B 18/14; A61B 2017/00557; A61B 17/3468; A61B 17/7065; A61B 17/00234; A61B 17/0401; A61B 17/221; A61B 17/32056; A61B 17/3478; A61B 17/66; A61B 17/70; A61B 17/7098; A61B 17/82; A61B 18/1442; A61H 2201/0207
USPC .................................. 602/13; 482/112, 140
See application file for complete search history.

(56) References Cited

U.S. PATENT DOCUMENTS

| 4,178,922 A | 12/1979 | Curlee |
| 4,178,923 A | 12/1979 | Curlee |
| 4,622,957 A | 11/1986 | Curlee |
| 4,682,587 A | 7/1987 | Curlee |
| 4,682,588 A | 7/1987 | Curlee |
| 4,702,235 A | 10/1987 | Hong |
| 4,756,306 A | 7/1988 | Curlee |
| 4,991,573 A | 2/1991 | Miller |
| 5,122,111 A | 6/1992 | Sebastian et al. |
| 5,179,942 A | 1/1993 | Drulias et al. |
| 5,188,585 A | 2/1993 | Peters |
| 5,205,814 A | 4/1993 | Lundrigan et al. |
| 5,349,706 A | 9/1994 | Keer |
| 2003/0125650 A1* | 7/2003 | Grosso ........................... 602/13 |
| 2005/0170938 A1* | 8/2005 | Parise ........................... 482/140 |

\* cited by examiner

*Primary Examiner* — Michael Brown
(74) *Attorney, Agent, or Firm* — Iandiorio Teska & Coleman, LLP

(57) ABSTRACT

A compression wrap for the lumbar spine region includes an elongate longitudinally stretchable belt for wrapping around the lumbar region of a person, a fastening device for securing the belt, a pressure pad extending transverse to the belt longitudinally along the spinous process and extending laterally in the hollow between the para-vertebral spinal muscles for applying support directly to the lumbar spine.

38 Claims, 8 Drawing Sheets

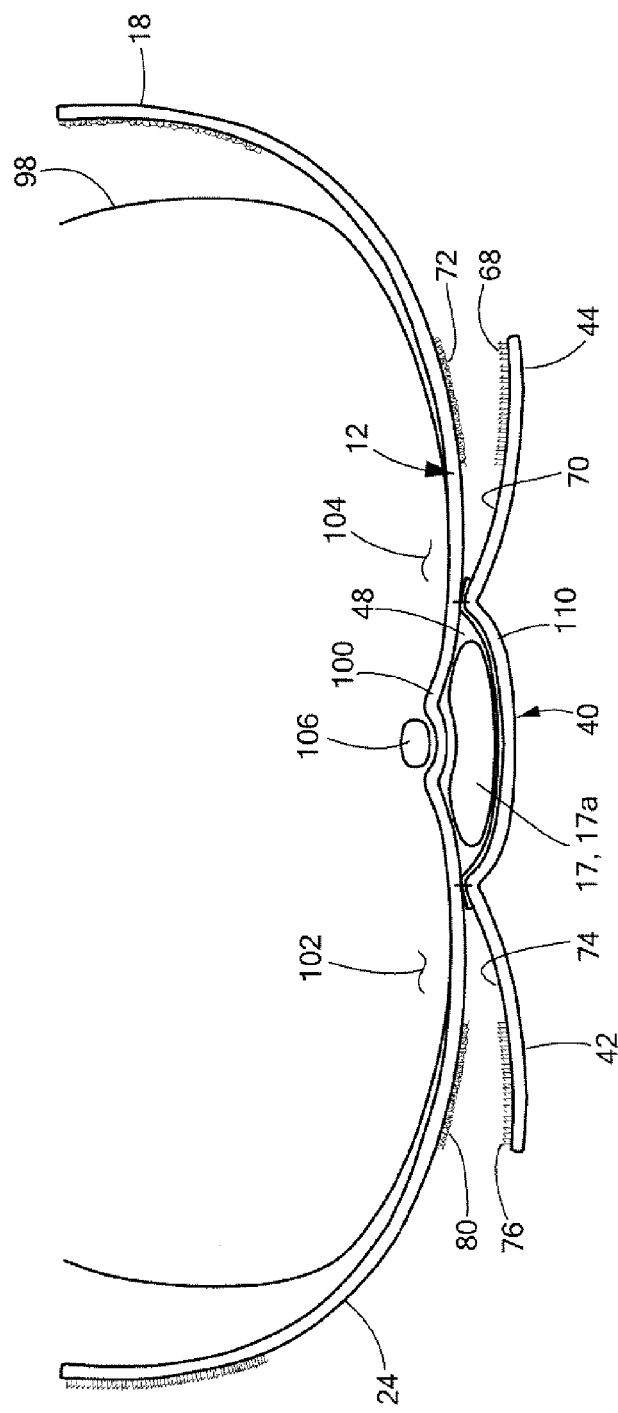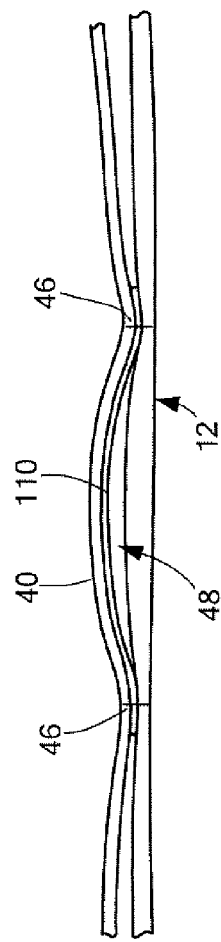
FIG. 4
FIG. 5

INFLATABLE COMPRESSION WRAP FOR DIRECT SUPPORT OF THE SPINOUS PROCESS IN THE LUMBAR SPECIFIC SPINE REGION

FIELD OF THE INVENTION

This invention relates to an improved compression wrap for the lumbar spine region, and more particularly to such a wrap for directly supporting the spinous process between the para-vertebral spinal muscles.

BACKGROUND OF THE INVENTION

Performance enhancing and therapeutic compression wraps for the lower backs in the lumbar region generally are in the form of elongate longitudinally stretchable belts. The belts may be elastic, inflatable or both. The belt is drawn tight around the waist using clips, ties, Velcro fasteners or other similar means. This form of compression does work to some extent to enhance performance of athletes, exercise participants and physical laborers, and for therapeutic and rehabilitation purposes. However, while these conventional wraps do give some support to the surrounding musculature, they do not specifically support the spinous processes, and therefore the spine, directly, in the lumbar region. This is so because the erectae spinae muscle group, the para-vertebral spinal muscles that border on each side of the spine are present in ridges which create a valley over the spine. The lumbar spine has to be supported in order to maintain the lordosis for proper weight support distribution of body weight and body biomechanics. Lordosis is a natural biomechanical shock absorber. The posterior movement seen in malpositioning of the lumbar spine is the cause of muscle splinting and pain. Thus there is a need for direct support of the spine to give relief and allow more normal function.

SUMMARY OF THE INVENTION

It is therefore an object of this invention to provide an improved compression wrap for the lumbar region.

It is a further object of this invention to provide such an improved compression wrap which provides specific support to the spinous processes between the para-vertebral spinal muscles in the lumbar region.

It is a further object of this invention to provide such an improved compression wrap which conforms closely to the body contours.

It is a further object of this invention to provide such an improved compression wrap which is easy to use and comfortable to wear.

It is a further object of this invention to provide such an improved compression wrap which is adjustable to provide the support necessary and appropriate for different individuals and activities.

It is a further object of this invention to provide such an improved compression wrap which does not interfere with the user's mobility or motion.

It is a further object of this invention to provide such an improved compression wrap which supports and helps maintain the normal lumbar lordosis through the full range of motion and activity.

It is a further object of this invention to provide such an improved compression wrap which is multipart and separable for washing and re-use.

It is a further object of this invention not to have to remove the whole belt when the increased lumbar support is not needed, but just to reduce the pressure in the bladder.

It is a further object of this invention that the support can be worn directly on the skin and under clothing.

It is a further object of this invention to have it made of such a fabric that that which contacts the skin wicks the potential moisture created by the increased muscle use.

The invention results from the realization that a truly effective compression wrap for the lumbar region can be achieved by using an elongate belt which is stretchable at least in the longitudinal direction for closely conforming to the body of the wearer and having a pressure pad for specifically engaging and supporting the lumbar spinous processes, the para-vertebral spinal muscles.

This invention features a compression wrap for the lumbar spine region including an elongate longitudinally stretchable belt for wrapping around the lumbar region of a person, fastening device for securing the belt, a pressure pad extending transverse to the belt longitudinally along the spinous process and extending laterally in the hollow between the para-vertebral spinal muscles for applying support directly to the lumbar spine.

In a preferred embodiment the belt includes a pocket for receiving the pad. The pad may include an inflatable bladder. The pocket may have an inner wall formed from stretchable material for engaging the lumbar region and an outer wall formed from a non-elastic web for constraining the expansion of the bladder inwardly directly against the lumbar region. The belt may be transversely as well as longitudinally stretchable to permit the belt to conform to the contours of the body throughout the range of motion. The fastening device may include a Velcro fastener with the hook portion on one end of the belt and the loop portion on the other. The compression wrap may further include a longitudinally stretchable reinforcing cinch mounted on the belt and covering the outside of the pad for compelling the pad to press specifically on the spinous processes of the lumbar region. The cinch may include left and right tabs, and a securing device associated with each the tab for securing it in the stretched condition to the belt for increasing the conformity of the belt, and pad to the lumbar region within the para-vertebral spine muscles. The tabs may be generally narrower than the belt. The securing devices may include Velcro fasteners. The bladder may be adjustably inflatable. The bladder may be sized to conform to the hollow between the para-vertebral muscles in the lumbar region. The bladder may be four to seven inches long and one to three inches wide. The pocket may be disposed in the belt. The inner wall of the pocket may be formed from the belt. The wrap may include a longitudinally stretchable reinforcing cinch mounted on the belt and covering the outside of the pocket for compelling the pad to press specifically on the spinous processes of the lumbar region between the para-vertebral spine muscles. The cinch may be permanently mounted to the belt. The cinch may be separably mounted to the belt. The wrap may include a longitudinal reinforcing cinch mounted on the belt and the pocket is formed by and between the belt and cinch. The cinch may be longitudinally generally stretchable. The inner wall of the pocket may be formed from the belt. The outer wall of the pocket may be formed from the cinch. The portion of the cinch forming the outer wall of the pocket may be generally stiff. The wrap may further include a stiffening member adopted for mounting in the pocket between the bladder and the cinch to constrain the bladder to exert more force upwardly against the spine of the wearer. The cinch may be permanently mounted to the belt. The cinch may be separably mounted to the belt. The wrap may include a longitudinally stretchable reinforcing cinch mounted on the belt and the pocket is formed in the cinch. The cinch may be permanently mounted to the belt. The cinch may be separably mounted to the belt. The wrap may include a pump and a tube interconnecting the pump and bladder. The tube may be serpentine shaped for permitting it to extend when the wrap is stretched. The pocket may be open on one side. The pocket may be closed.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 4 is a top plan view of the wrap of FIG. 1 showing the manner in which the inflatable bladder conforms and supports the spinous processes in the lumbar region;

FIG. 5 is an enlarged detailed top plan view of a portion of the compression wrap of FIG. 1 showing the pocket for containing the inflatable bladder;

DETAILED DESCRIPTION OF THE INVENTION

Figure 1:
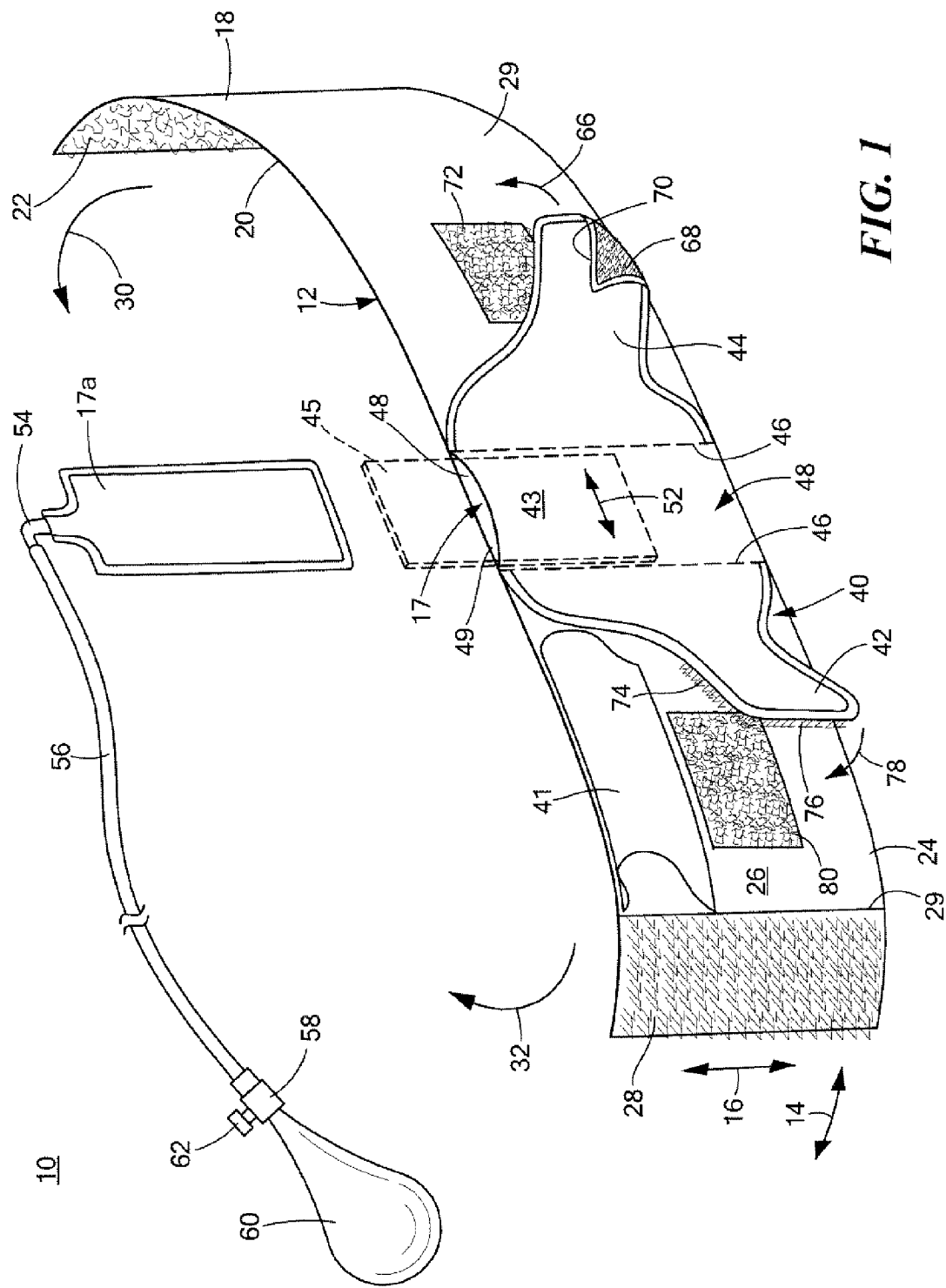
FIG. 1 is a three-dimensional diagrammatic view of a compression wrap according to this invention with the inflatable bladder removed for clarity.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

There is shown in FIG. 1 a compression wrap 10 according to this invention including a belt 12 which is stretchable in two directions in the longitudinal direction, arrow 14, and the lateral direction, arrow 16. There is a pressure pad 17 extending transverse to belt 12, longitudinally along the spinous processes and extending laterally in the hollow between the para-vertebral spinal muscles of the erectae spinae for applying support directly to the spinous processes in the lumbar region. The right hand section 18 of belt 12 includes on its inside surface 20 one portion, either the hook or loop portion, of a Velcro fastener 22. The left hand section 24 of belt 12 includes on its outside surface 26 the complementary hook and loop portion 28 of the Velcro fastener. Thus when the belt is wrapped around the person's waist as indicated by arrows 30, 32, the right hand section 18 overlaps left hand section 24 so that Velcro portion 22 laps over and engages with Velcro portion 28 to secure the belt in place and tightly and snugly conform it to the body contours of the wearer. Velcro sections 22 and 28 may be attached by stitching such as shown at 29, bonding, or any other suitable technique.

Wrap 10 also includes a reinforcing cinch 40 including a left tab 42 and right tab 44. Reinforcing cinch 40 is stitched such as by stitches 46 to belt 12 so as to form a pocket 48 into which pad 17 may be inserted. Pad 17 may be a cushion like material such as foam rubber or may be a bladder filled with air or some other fluid. Preferably pad 17 could be implemented with an inflatable bladder 17a. Bladder 17a may be housed on wrap 10 in longitudinal pocket 41. Pocket 48 may have stitches at 46 and 49 so it is a closed pocket or may have stitches only at 46 so the top is open. Reinforcing cinch 40 may be stretchable in at least the longitudinal direction as indicated by arrow 52. In a preferred embodiment the position 43 of reinforcing cinch 40 between stitches 46 that form the back side of pocket 48 may be made of material which is non-stretchable, stiff or rigid to compel bladder 17a when against the back of the wearer for increased pressure and support. Alternately, or in addition a stiffener such as a hard plastic plate 45 in pocket 48 between position 43 and bladder 17a. Inflatable bladder 17a is inflated through fixture 54, tube 56 and valve mechanism 58 by means of syringe 60. The level of inflation of bladder 17a is controlled by the combination of syringe 60 which increases the pressure and valve 58 which holds the pressure and can be used to decrease it via valve actuator 62. Cinch 40 can be used to enhance and increase the conformance of belt 12 to the body of the wearer. After the belt is installed, right hand tab 44 is pulled tightly in the direction shown by arrow 66 and Velcro section 68 on the inside surface 70 of right tab 44 is securely fastened to the mating Velcro pad 72 mounted on belt 12. In similar fashion, left hand tab 42 carries on its inside surface 74 Velcro section 76 which when tab 42 is pulled tightly in the direction of arrow 78 engages and securely fastens to Velcro pad 80 attached on the left hand side of belt 12.

Figure 2:
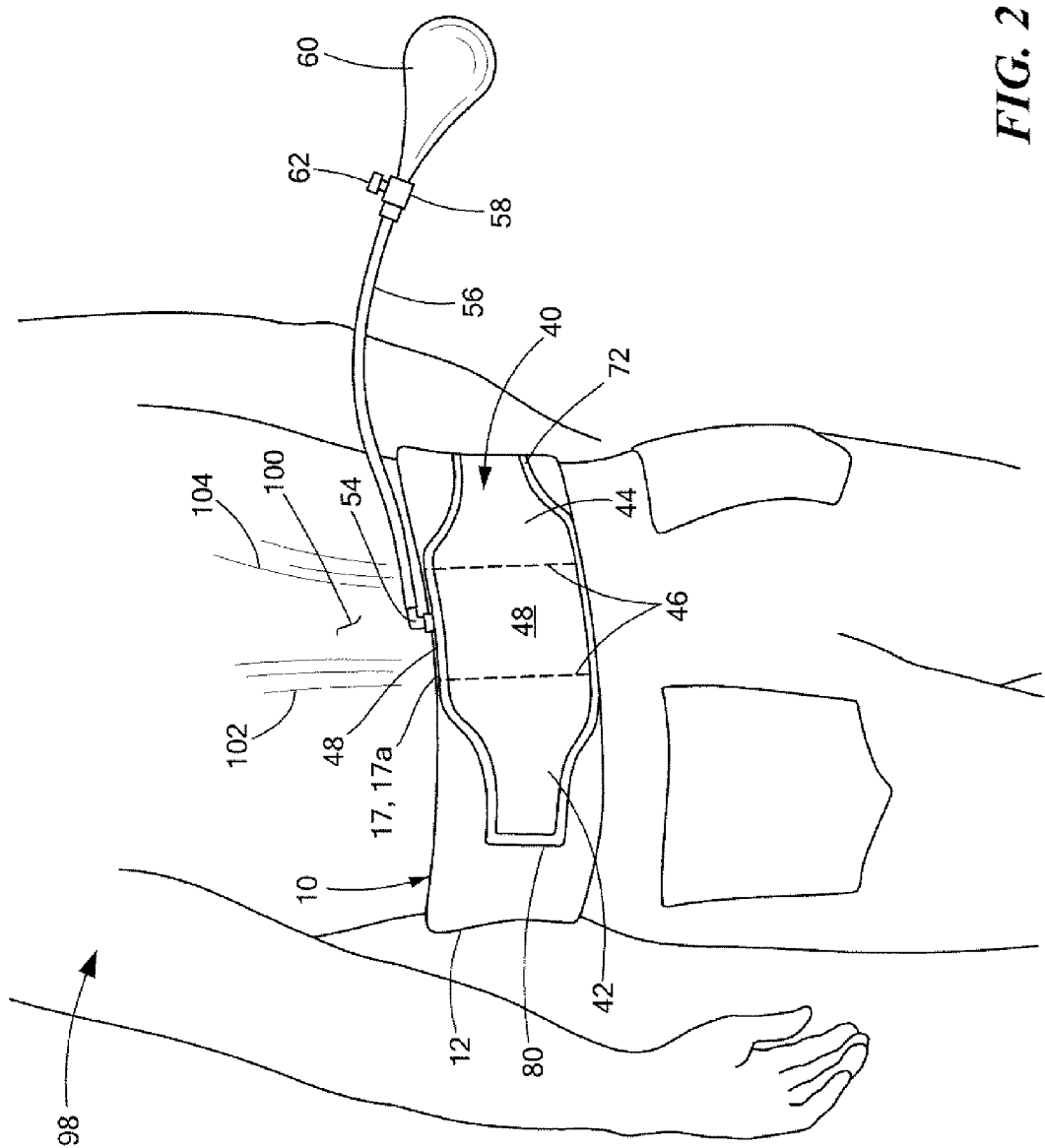
FIG. 2 is a back view of the compression wrap of FIG. 1 in place on a person with the bladder inserted in the pocket.

Wrap 10 is shown fully installed with belt 12, FIG. 2, tightly wrapped around the body of the wearer 98 and reinforcing cinch 40 engaged. Inflatable bladder 17a is installed in pocket 48 and is inflated to fully engage and support the spinae processes in the hollow 100 created between the para-vertebral erectae spinae muscles 102, 104 of the wearer 98.

Figure 3:
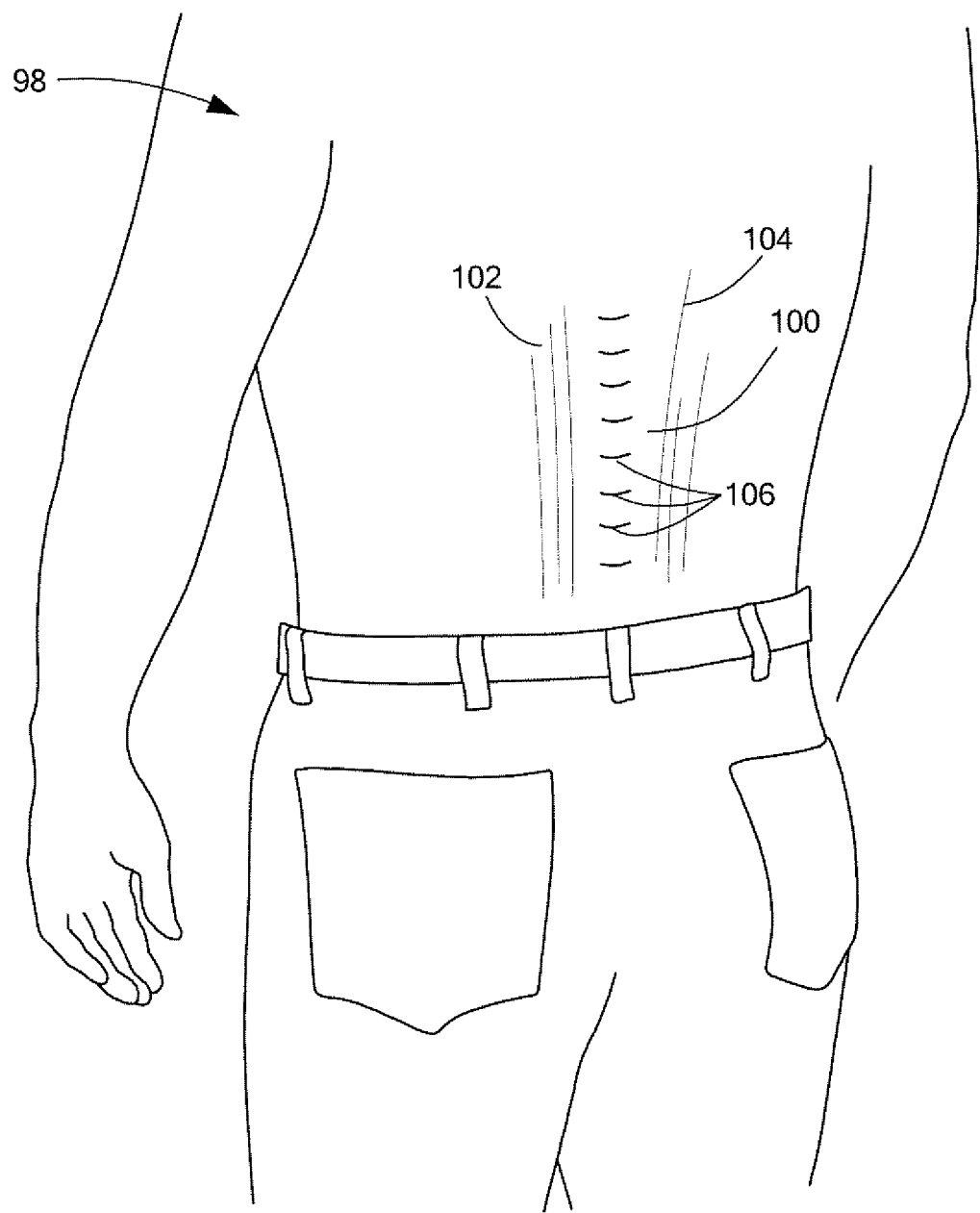
FIG. 3 is a view similar to FIG. 2 of a person with the compression wrap removed showing the structure of the spine and the erectae spinae which form the hollow in the lumbar spine area.

The anatomy referred to is depicted more clearly in FIG. 3, where the wearer 98 is shown with the belt removed so that the hollow 100 between the erectae spinae muscles 102 and 104 are more clearly shown along with the spinae processes 106.

Figure 6:
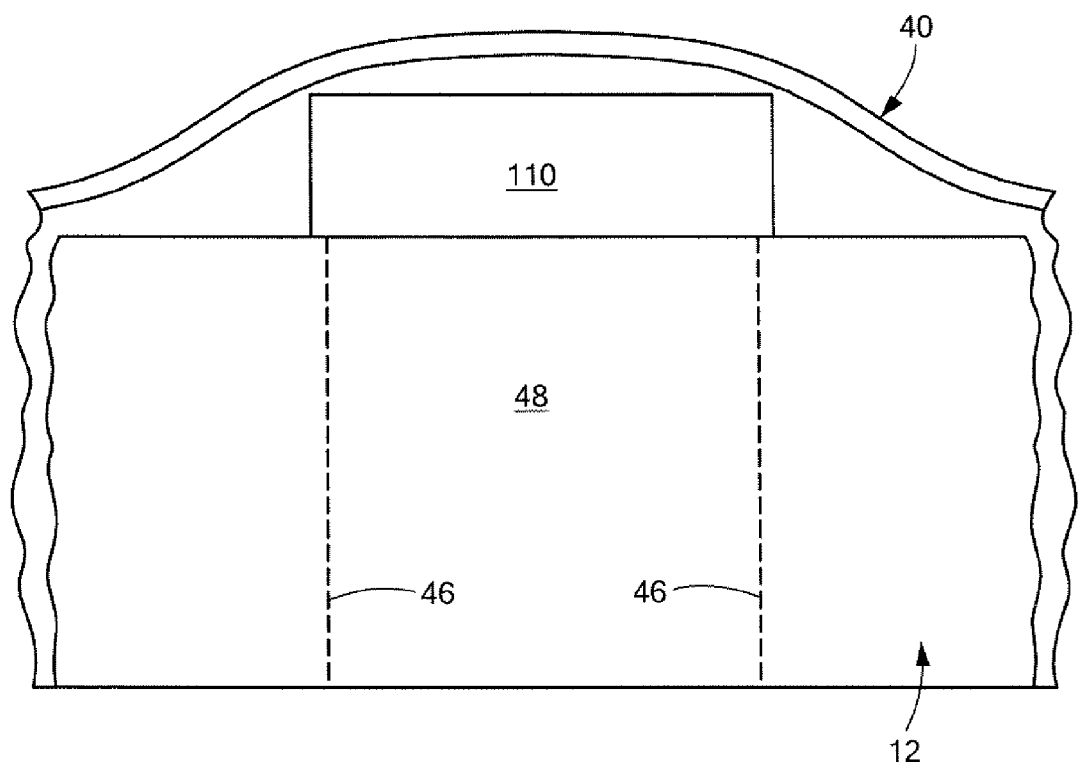
FIG. 6 is an exploded three-dimensional view showing the three-ply construction of the pocket.
Figure 7:
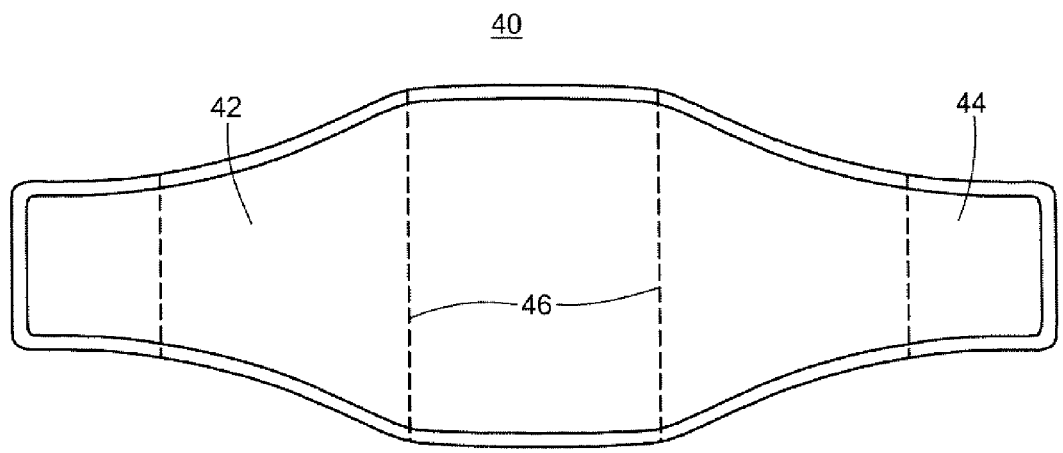
FIG. 7 is a rear view of the reinforcing cinch of FIG. 1.
Figure 8:
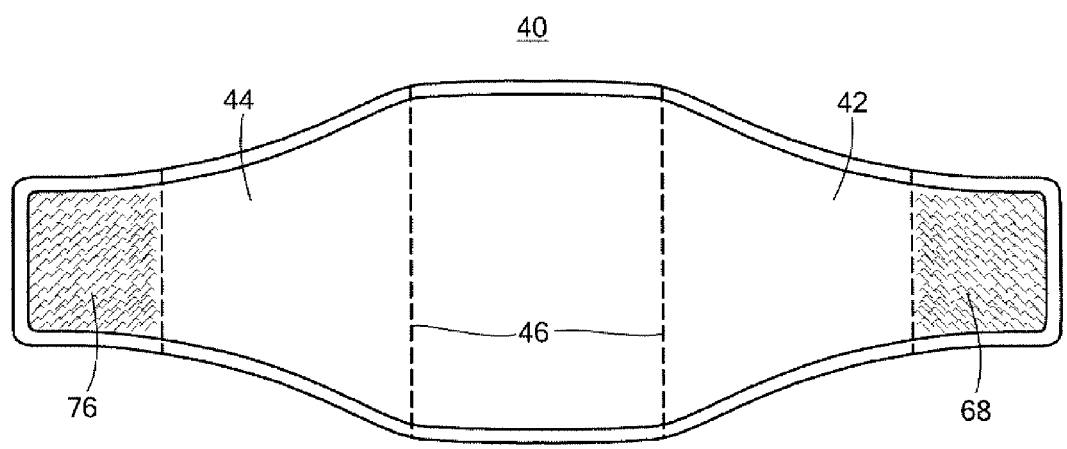
FIG. 8 is a front view of the cinch of FIG. 7 showing the Velcro fasteners which attach to similar fasteners on the belt.

The pocket 48 is shown to greater advantage in FIG. 4, where it is seen as having its inner wall formed from the dually stretchable material of belt 12 while the outer wall is formed by reinforcing cinch 40. The outer wall is lined with a non-stretchable webbing 110 which insures that the force developed from the inflation of inflatable bladder 17a is directed mainly against the spinae processes 102 and not against the stretchable belt 12 or cinch 40. The construction of pocket 48 can be seen with greater clarity in FIGS. 5 and 6, where it is apparent that the stitching 46 that forms pocket 48 engages cinch 40 and webbing 110 as well as belt 12. A clearer view of reinforcing cinch 40 is shown in FIGS. 7 and 8, where FIG. 7 is the rear view facing away from belt 12 and FIG. 8 is a front view of the portion that faces, is stitched to and engages belt 12.

Figure 9:
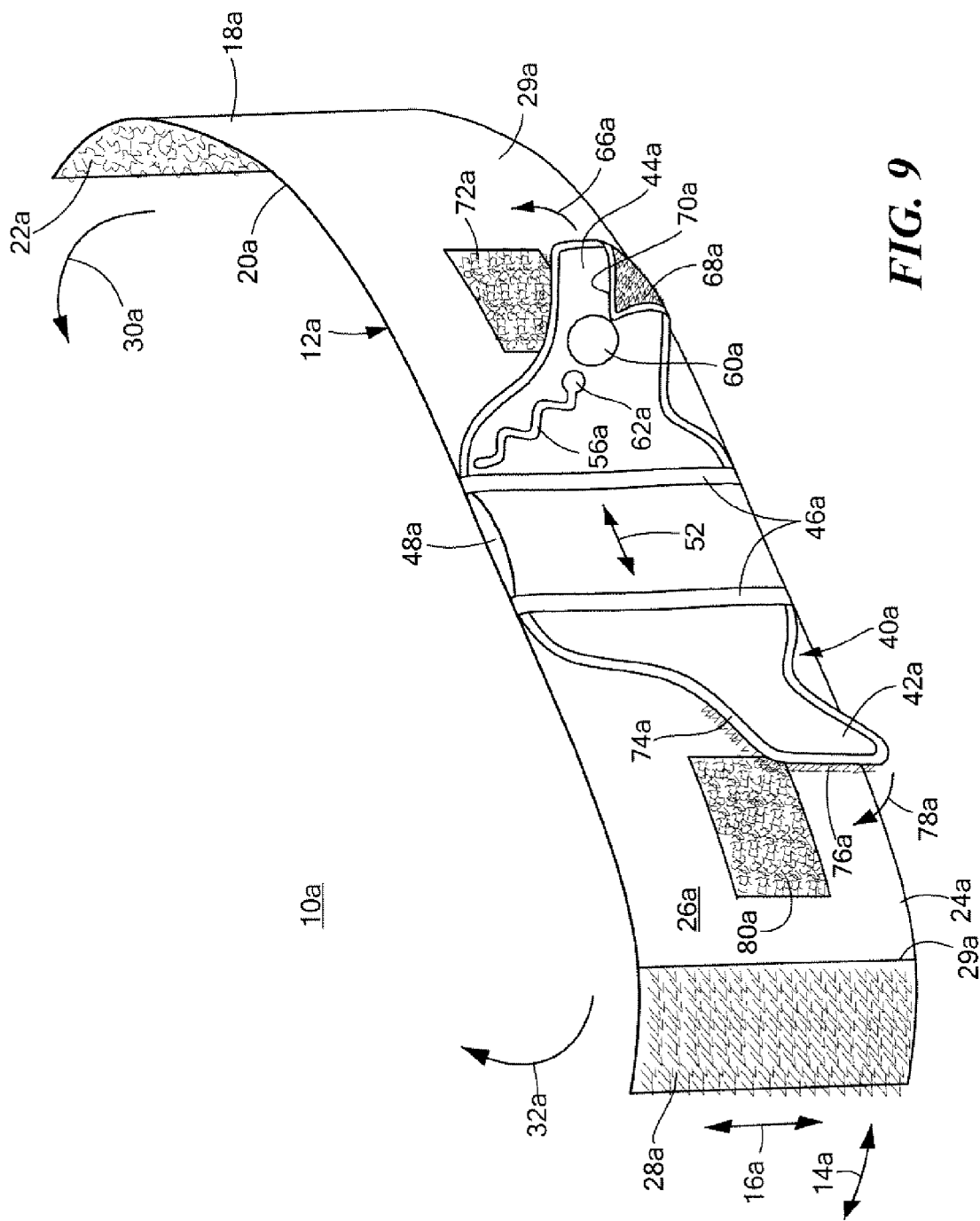
FIG. 9 is a three-dimensional diagrammatic view of an alternative compression wrap according to this invention with the inflatable bladder housed in a separable cinch.
Figure 10:
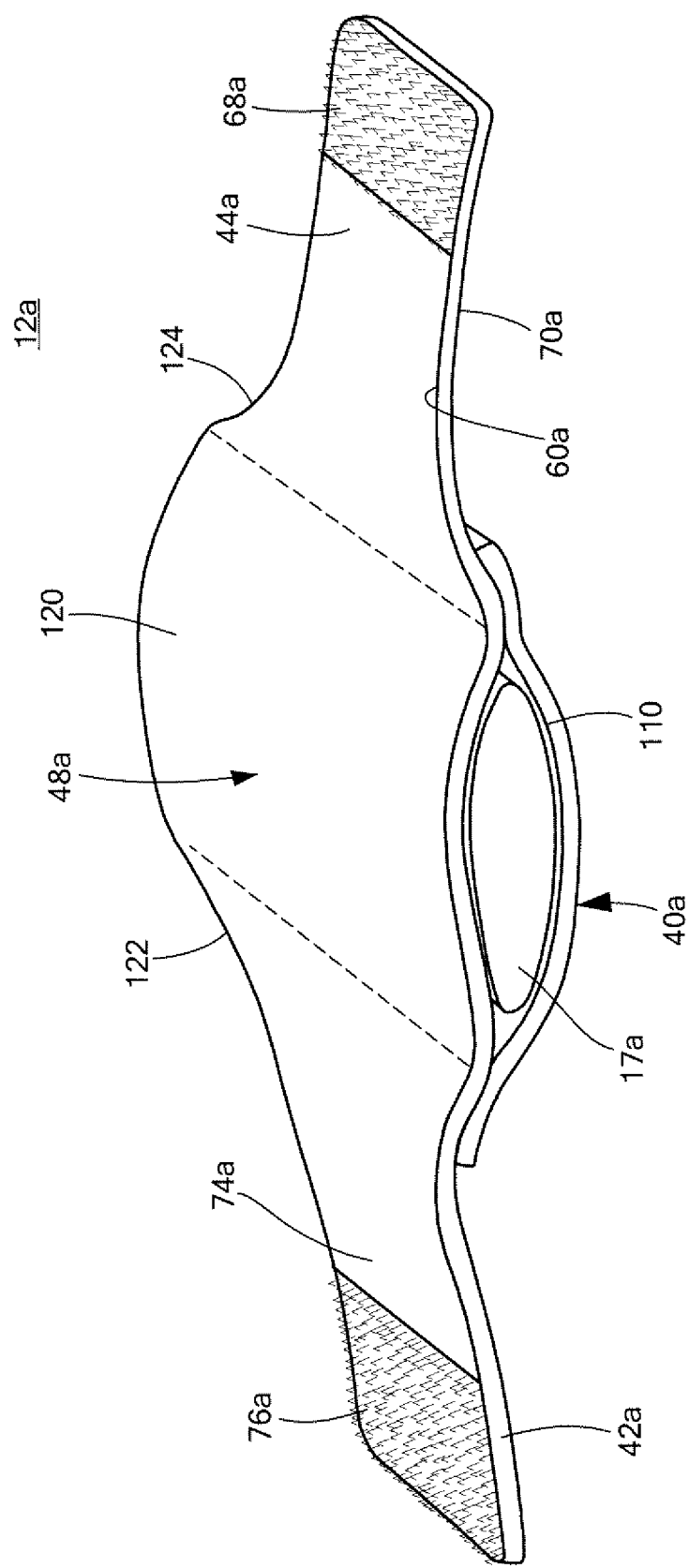
FIG. 10 is a three-dimensional view of the separable cinch of FIG. 9.

In another construction, FIG. 9, the pocket 48a for holding the bladder 17a is contained wholly in cinch 40a so belt 12a can be removed and separately washed for reuse. In this embodiment cinch 40a is not stitched to belt 12a but is held in place by belt loops 46a from which cinch 40a can be easily slid out to separate from belt 12a. Cinch 40a, FIG. 10, is provided with an inner section 120 made of stretchable material such as that of belt 12a to make pocket 48a which is stretchable on the side toward the wearer so that bladder 17a can readily expand in that direction while being constrained in the other direction by cinch 40a. Section 120 is secured such as by threads 122 and 124. Tube 56a has a serpentine shape to allow it to extend when belt 120 and cinch 40a are stretched. The belt not only supports the lumbar curve by placing direct contact pressure to the spine but also provides the supporting muscles a fixture again which they can "push" to create additional support.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A compression wrap for the lumbar spine region comprising:
    an elongate longitudinally stretchable belt for wrapping around the lumbar region of a person;
    a fastening device for securing said belt;
    a rear pressure pad extending transverse to said belt longitudinally along the spinous process and extending laterally in the hollow between the para-vertebral spinal muscles for applying support directly to the lumbar spine; and
    a longitudinally stretchable reinforcing cinch mounted on said belt and covering the outside of said pad for compelling said pad to press specifically on the spinous processes of the lumbar region.

2. The compression wrap of claim 1 in which said belt includes a pocket for receiving said pad.

3. The compression wrap of claim 2 in which said pad includes an inflatable bladder.

4. The compression wrap of claim 3 in which said bladder is adjustably inflatable.

5. The compression wrap of claim 3 in which said wrap includes a pump and a tube interconnecting said pump and bladder.

6. The compression wrap of claim 5 in which said tube is serpentine shaped for permitting it to extend when the wrap is stretched.

7. The compression wrap of claim 3 in which said bladder is four to seven inches long and one to three inches wide.

8. The compression wrap of claim 2 in which said pocket has an inner wall formed from stretchable material for engaging the lumbar region and an outer wall formed from a non-elastic plate for constraining the expansion of said bladder outwardly and directing it inwardly against the lumbar region.

9. The compression wrap of claim 2 in which said pocket is disposed in said belt.

10. The compression wrap of claim 9 in which said inner wall of said pocket is formed from said belt.

11. The compression wrap of claim 2 in which said longitudinally stretchable reinforcing cinch mounted on said belt is covering the outside of said pocket for compelling said pad to press specifically on the spinous processes of the lumbar region between said para-vertebral spine muscles.

12. The compression wrap of claim 11 in which said cinch is permanently mounted to said belt.

13. The compression wrap of claim 11 in which said cinch is separably mounted to said belt.

14. The compression wrap of claim 2 in which said wrap includes a longitudinal reinforcing cinch mounted on said belt and said pocket is formed by and between said belt and cinch.

15. The compression wrap of claim 14 in which said cinch is longitudinally generally stretchable.

16. The compression wrap of claim 14 in which said inner wall of said pocket is formed from said belt.

17. The compression wrap of claim 16 in which said outer wall of said pocket is formed from said cinch.

18. The compression wrap of claim 17 in which the portion of said cinch forming said outer wall of said pocket is generally stiff.

19. The compression wrap of claim 17 in which said wrap further includes a stiffening member adopted for mounting in said pocket between said bladder and said cinch to constrain said bladder to exert more force inwardly against the spine of the wearer.

20. The compression wrap of claim 14 in which said cinch is permanently mounted to said belt.

21. The compression wrap of claim 14 in which said cinch is separably mounted to said belt.

22. The compression wrap of claim 2 in which said pocket is formed in said cinch.

23. The compression wrap of claim 22 in which said cinch is permanently mounted to said belt.

24. The compression wrap of claim 22 in which said cinch is separably mounted to said belt.

25. The compression wrap of claim 1 in which said belt is transversely as well as longitudinally stretchable to permit said belt to conform to the contours of the body throughout the range of motion.

26. The compression wrap of claim 1 in which said fastening device includes a hook and loop fastener with the hook portion on one end of the belt and the loop portion on the other.

27. The compression wrap of claim 1 in which said cinch includes left and right tabs, and a securing device associated with each said tab for securing it in the stretched condition to said belt for increasing the conformity of said belt, and pad to the lumbar region within said para-vertebral spine muscles.

28. The compression wrap of claim 27 in which said tabs are generally narrower than said belt.

29. The compression wrap of claim 27 in which said securing devices include Velcro fasteners.

30. The compression wrap of claim 1 in which said bladder is sized to conform to the hollow between the para-vertebral muscles in the lumbar region.

31. The compression wrap of claim 2 in which said pocket is open on one side.

32. The compression wrap of claim 2 in which said pocket is closed.

33. A compression wrap for the lumbar spine region comprising:
  an elongate longitudinally stretchable belt for wrapping around the lumbar region of a person;
  a fastening device for securing said belt;
  a pressure pad extending transverse to said belt longitudinally along the spinous process and extending laterally in the hollow between the para-vertebral spinal muscles for applying support directly to the lumbar spine; and
  a longitudinally stretchable reinforcing cinch mounted on said belt for compelling said pad to press specifically on the spinous processes of the lumbar region.

34. The compression wrap of claim 33 in which said cinch includes left and right tabs, and a securing device associated with each said tab for securing it in the stretched condition to said belt for increasing the conformity of said belt, and pad to the lumbar region within said para-vertebral spine muscles.

35. The compression wrap of claim 34 in which said tabs are generally narrower than said belt.

36. The compression wrap of claim 34 in which said securing devices include Velcro fasteners.

37. A compression wrap for the lumbar spine region comprising:
  an elongate longitudinally stretchable belt for wrapping around the lumbar region of a person, said belt including a pocket;
  a fastening device for securing said belt;
  a pressure pad in said pocket and extending transverse to said belt longitudinally along the spinous process and extending laterally in the hollow between the para-vertebral spinal muscles for applying support directly to the lumbar spine; and
  a longitudinally stretchable reinforcing cinch mounted on said belt and covering the outside of said pocket for compelling said pad to press specifically on the spinous processes of the lumbar region between said para-vertebral spine muscles.

38. A compression wrap for the lumbar spine region comprising:
  an elongate longitudinally stretchable belt for wrapping around the lumbar region of a person, said belt including a pocket;
  a fastening device for securing said belt;
  a pressure pad in said pocket extending transverse to said belt longitudinally along the spinous process and extending laterally in the hollow between the para-vertebral spinal muscles for applying support directly to the lumbar spine; and
  a longitudinal reinforcing cinch mounted on said belt and said pocket is formed by and between said belt and cinch.

* * * * *